United States Patent [19]

Pirkle

[11] 4,119,903
[45] Oct. 10, 1978

[54] DEFIBRILLATOR CHARGING CIRCUIT

[75] Inventor: Sherman Jack Pirkle, Waltham, Mass.

[73] Assignee: Hewlett-Packard Company, Palo Alto, Calif.

[21] Appl. No.: 867,263

[22] Filed: Jan. 5, 1978

[51] Int. Cl.² ................... H02M 9/04; A61N 1/38
[52] U.S. Cl. .................................... 320/1; 128/419 D
[58] Field of Search ..................... 320/1; 128/419 D

[56] References Cited

U.S. PATENT DOCUMENTS

| 3,527,228 | 9/1970 | McLaughlin | 128/419 D |
| 3,721,884 | 3/1973 | Thakore | 320/1 |
| 3,721,885 | 3/1973 | McKeown et al. | 320/1 |

Primary Examiner—Stuart N. Hecker
Attorney, Agent, or Firm—Donald N. Timbie

[57] ABSTRACT

Change in the charge level of a storage capacitor of a defibrillator is accomplished by setting the charge control to the new level and successively closing and opening the charge switch. This actuates the safety relay so as to remove a low impedance shunt from the capacitor and it initiates the charging action. Charging ceases when the preset charge level is reached.

1 Claim, 1 Drawing Figure

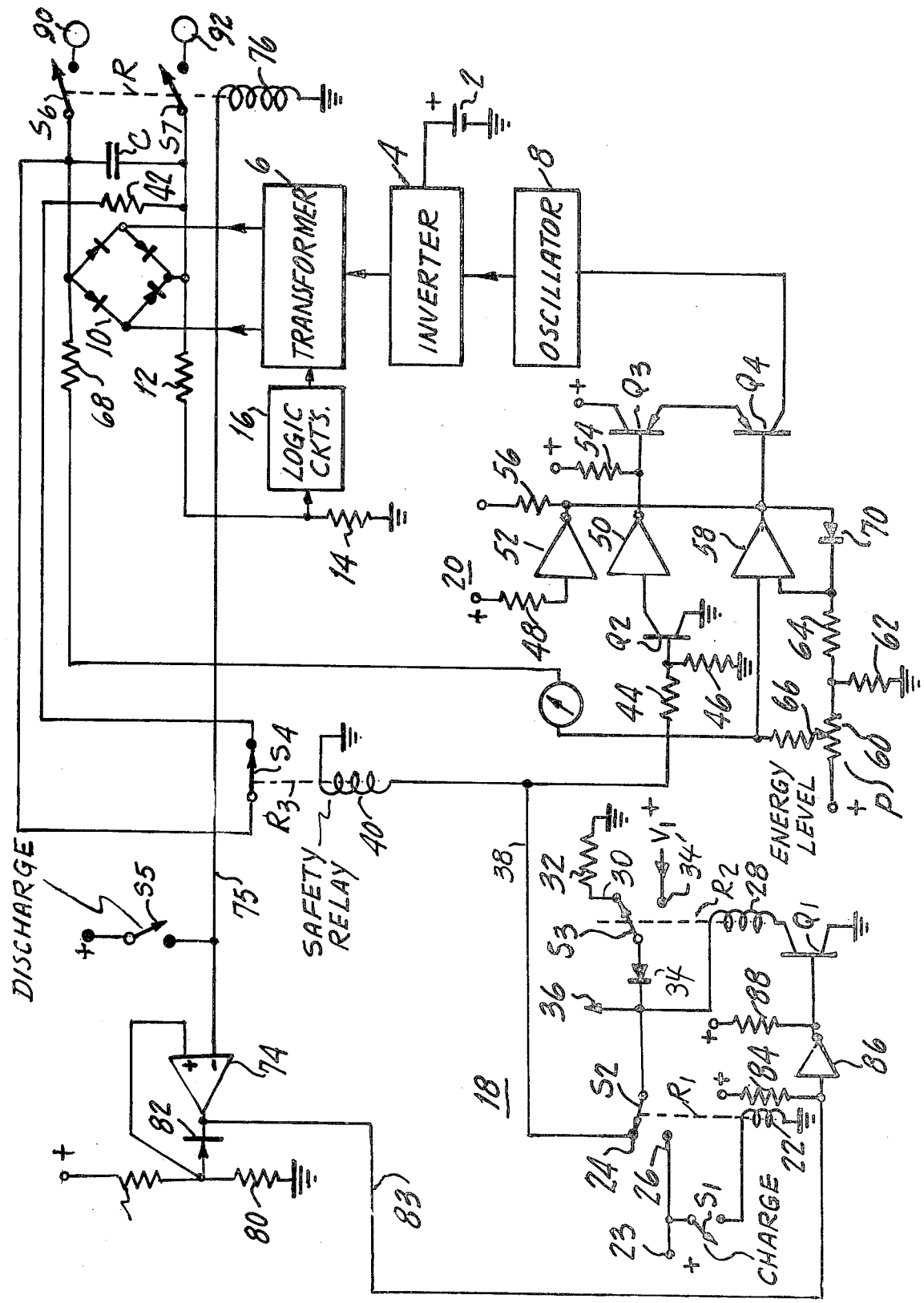

DEFIBRILLATOR CHARGING CIRCUIT

BACKGROUND OF THE INVENTION

Defibrillators restore a patient's heart to normal operation by discharging a storage capacitor through paddle electrodes held against the chest. Inasmuch as they are only used is life-or-death situations where time is of the essence, it is imperative that their operation be made as simple as possible. It is often necessary to change the amount of charge on the capacitor before discharging it. In present equipment, this is done by bringing the paddle electrodes together so as to discharge the capacitor, setting the charge control to a desired charge level, and initiating the charging action by depressing a charge button. When the desired energy level is reached, charging is terminated.

BRIEF DESCRIPTION OF THE DRAWING

The FIGURE illistrates an exemplary embodiment of the invention.

BRIEF DISCUSSION OF THE INVENTION

In accordance with this invention, readjustment of the desired level to which the capacitor is charged is achieved by simply setting the charge level control to the desired value and depressing and releasing the charge initiating switch. When it is depressed, the safety relay is de-energized so as to place a low impedance in shunt across the capacitor, thereby discharging it. When the switch is released, the safety relay is energized so as to remove the low impedance shunt and start the charging of the capacitor. When the desired level of charge is reached, the charging action automatically ceases.

In a defibrillator utilizing this invention, the storage capacitor may be charged in any manner, but as generally illustrated in the drawing, the storage capacitor C is shown as being charged in a manner set forth in my U.S. Patent application, Ser. No. 839,076, entitled "Capacitor Charging Circuit", filed on Oct. 3, 1977. The battery 2 is coupled to an inverter 4 that is caused to produce pulses of current in the primary windings, not shown, of a transformer 6 under the control of an oscillator 8. The secondary winding, also not shown, of the transformer 6 is coupled to one diagonal of a full wave rectifier bridge circuit 10, and the capacitor C is connected across the other diagonal. Resistors 12 and 14 are connected in series between one side of the capacitor C and grond so as to provide a voltage at their junction that is small enough for application to logic circuits 16. In a manner explained in the aforesaid patent application, the logic circuits 16 increase the turns ratio between the secondary and primary windings of the transformer 6 whenever the voltage on the capacitor C increases through predetermined levels.

Charging of the capacitor C is initiated by closing and opening a charge switch $S_1$ in a circuit generally indicated by the number 18, and the voltage to which the capacitor is charged is determined by the setting of a potentiometer P in a charge level control circuit generally indicated by the number 20. The detailed operation of the circuit 18 is as follows. Closing of the switch $S_1$ applies a positive potential at a terminal 23 to the ungrounded end of a coil 22 of a relay $R_1$ causing its armature $S_2$ to move from the illustrated position, wherein it is in contact with a terminal 24, to a position wherein it is in contact with a terminal 26. The terminal 26 is connected to the terminal 23 so that a positive voltage is applied via the armature $S_2$ to one end of a coil 28 of a relay $R_2$. The other end of the coil 28 is connected to the emitter of a PNP transistor $Q_1$, and its collector is connected to ground. For reasons that will be explained, the base of the transistor $Q_1$ is normally at a low voltage so that it conducts, causing the relay $R_2$ to move its armature $S_3$ from a position shown, wherein it is in contact with a terminal 30 that is grounded via a resistor 32, to a position wherein it is in contact with a terminal 34 to which a positive voltage $V_1$ is applied.

Opening the switch $S_1$ de-energizes the coil 22 of the relay $R_1$ so as to permit its armature $S_2$ to return to the position shown, but the relay $R_2$ is latched by the application of the voltage $V_1$ to the ungrounded end of the relay coil 28 via the armature $S_3$ and diode 34. The voltage $V_1$ is applied via a bus 36 to provide power to other circuits. It is also applied via the switch $S_2$ and a lead 38 to the ungrounded end of a coil 40 so as to energize a safety relay $R_3$. When the relay $R_3$ is de-energized, its armature $S_4$ connects a resistor 42 of low value across the capacitor C as shown so as to keep it in a discharge condition until the defibrillator is to be used and the charging switch $S_1$ is closed. When the relay $R_3$ is energized, $S_4$ opens and removes the resistor 42 from the circuit so that the capacitor C can be charged.

The energy level control circuit 20 will now be described. Resistors 44 and 46 are connected in series between the lead 38 and ground, and their junction is connected to the base of an NPN transistor $Q_2$. Its collector is connected to a point of positive voltage via a resistor 48, and its emitter is connected to the inputs of two inverting open collector amplifiers 50 and 52. Their outputs are connected via resistors 54 and 56 respectively to points of positive potential. The output of the amplifier 50 is connected to the base of an NPN transistor $Q_3$, and the output of the amplifier 52 is connected to the base of a PNP transistor $Q_4$ and to the output of a comparator 58. The collector of transistor $Q_3$ is connected to a point of positive potential, and the emitters of transistors $Q_3$ and $Q_4$ are connected. When both transistors are conducting, operating potential is supplied to the oscillator 8 so that the capacitor C can be charged. But when either transistor is turned off, the oscillator 8 is turned off and charging ceases.

Selection of the voltage to which the capacitor C is to be charged is determined by the following circuit elements in the circuit 20. One end of a resistor 60 of the potentiometer P is connected to a point of positive potential, and the other end is connected to ground via a resistor 62. The junction of these resistors is connected via a resistor 64 to the non-inverting input of the comparator 58. A resistor 66 is connected in series with a resistor 68 between the arm of the potentiometer P and the side of the capacitor C opposite that to which the resistor 12 is connected. The junction of the resistors 66 and 68 is connected to the inverting input of the comparator 58. Before any charge is applied to the capacitor C, the inverting input of the comparator 58 is more positive than the non-inverting input, so that its output is low.

When no voltage is applied to the lead 38, i.e., before $S_1$ is closed, the transistor $Q_2$ is turned off, its output is high, and the outputs of the amplifiers 50 and 52 are low. Accordingly, the transistor $Q_4$ is biased for conduction and the transistor $Q_3$ is biased to cut off. The function of the amplifier 52 is to keep the output of the comparator 58 low, as otherwise it would be latched in a high state by current flowing through the resistor 56 and a diode 70 that has its anode connected to the output of the comparator 58 and its cathode connected to the non-inverting input.

When the voltage $V_1$ is applied to the lead 38 in the manner previously explained in connection with the circuit 18, the relay $R_3$ is energized, as just explained, and the transistor $Q_1$ conducts so as to effectively remove the amplifiers 50 and 52 from the circuit. Transistor $Q_3$ is now biased for conduction so that voltage is applied to the oscillator 8 enabling it to operate and commence the charging of the capacitor C. As this charging proceeds, the current through the resistor 66 reduces the positive voltage on the inverting input of the comparator 58. When this voltage equals the positive voltage applied to the non-inverting input, the output of the comparator 58 goes high, turning off transistor $Q_4$ and the oscillator 8. The charging of the capacitor C therefore stops at a potential determined by the setting of the arm of the potentiometer P. The potential is greater as the arm is moved toward the positive end of the resistor 60. The comparator 58 is latched by the diode 70.

The circuit for discharging the capacitor C is comprised of a comparator 74 having its inverting input connected via the lead 75 to the ungrounded end of a coil 76 of a patient relay $R_4$ and its non-inverting input connected to the junction of resistors 78 and 80 that are in series between a point of positive potential and ground. The anode of a latching diode 82 is connected to the junction of the resistors 78 and 80, and its cathode is connected to the output of the comparator 74. The output of the comparator is connected to a point of positive potential via lead 83 and a resistor 84 and to the input of an open collector inverting amplifier 86. The output of the amplifier 86 is connected to a point of positive potential via a resistor 88 and to the base of the transistor $Q_1$. A normally open discharge switch $S_5$ is connected between a point of positive potential and the lead 75.

When the switch $S_5$ is open, the voltage on the lead 83 is positive and the output of the amplifier 86 and the base of the transistor $Q_1$ are negative, so that the transistor $Q_1$ is biased for conduction. Momentary closing of the switch $S_5$ places a positive potential on the lead 75 so as to energize the coil 76 of the patient relay $R_4$ so as to close normally open switches $S_6$ and $S_7$ that are respectively connected between opposite sides of the storage capacitor C and paddle electrodes 90 and 92. The capacitor C then discharges through the portion of a patient's body between the paddle electrodes.

Momentary closing of the discharge switch $S_5$ also applies a positive potential to the inverting input of the comparator 74, causing its output to go negative and the output of the amplifier 86 to go positive. This cuts off transistor $Q_1$ so as to de-energize the coil 28 of the relay $R_2$ and cause its armature $S_3$ to return to the grounded position shown. No power is applied to the lead 38 or the circuit power bus 36. All circuits are then de-energized and the armature $S_4$ of the relay $R_3$ returns to its closed position so as to place the resistor 42 in shunt with the capacitor C.

What is claimed is :

1. In a defibrillator, a storage capacitor, a safety relay having an armature that is closed when said relay is de-energized, said armature, when closed, providing a low impedance discharge path for said storage capacitor, a battery, charging means coupled between said battery and said capacitor for charging said capacitor when said means is energized, said means being normally de-energized, a charge switch having one side connected to one side of said battery, means coupled between the other side of said switch for energizing said safety relay when said switch is closed so as to open its armature and remove the discharge path from said storage capacitor, and means responsive to the closure of said switch for energizing said charging means so as to cause it to charge said storage capacitor.

* * * * *